(12) United States Patent
Zwiefel et al.

(10) Patent No.: US 7,341,564 B2
(45) Date of Patent: Mar. 11, 2008

(54) BIOPSY FORCEPS DEVICE WITH TRANSPARENT OUTER SHEATH

(75) Inventors: Aaron Zwiefel, Sunrise, FL (US); John J. Damarati, Tokyo (JP); Masaru Yokomaku, Chiba (JP); Keisuke Hirai, Tokyo (JP); Hideko Goto, Tokyo (JP); Kumiko Tatami, Ishikawa (JP); Eiko Hikage, Tokyo (JP)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1052 days.

(21) Appl. No.: 10/132,879

(22) Filed: Apr. 24, 2002

(65) Prior Publication Data

US 2002/0165580 A1  Nov. 7, 2002

Related U.S. Application Data

(60) Provisional application No. 60/288,335, filed on May 3, 2001.

(51) Int. Cl.
*A61B 10/06* (2006.01)
(52) U.S. Cl. .................. 600/564; 606/46; 606/205
(58) Field of Classification Search ............ 606/170, 606/174, 205
See application file for complete search history.

(56) References Cited

U.S. PATENT DOCUMENTS

| | | | |
|---|---|---|---|
| 1,127,948 A | 2/1915 | Wappler | |
| 2,036,528 A | 4/1936 | Kesling | |
| 2,950,609 A | 8/1960 | Goodloe | |
| 3,529,633 A * | 9/1970 | Vaillancourt | 604/523 |
| 3,554,192 A | 1/1971 | Isberner | |
| 3,605,750 A * | 9/1971 | Sheridan et al. | 604/529 |
| 3,805,770 A | 4/1974 | Okada | |
| 3,895,636 A | 7/1975 | Schmidt | |
| 3,955,578 A | 5/1976 | Chamness et al. | |
| 4,256,113 A | 3/1981 | Chamness | |
| 4,294,254 A | 10/1981 | Chamness | |
| 4,306,546 A * | 12/1981 | Heine et al. | 600/160 |
| 4,326,530 A | 4/1982 | Fleury, Jr. | |
| 4,327,711 A | 5/1982 | Takagi | |
| 4,345,599 A | 8/1982 | McCarrell | |
| 4,430,083 A | 2/1984 | Ganz et al. | |

(Continued)

FOREIGN PATENT DOCUMENTS

DE    28 29 159 A1    1/1980

(Continued)

OTHER PUBLICATIONS http://www.texloc.com/tube_fep.html; "TEXfluor FEP Tubing".*

(Continued)

*Primary Examiner*—Glenn K. Dawson
(74) *Attorney, Agent, or Firm*—Crompton, Seager & Tufte, LLC

(57) ABSTRACT

An endoscopic biopsy device having an outer sheath that is transparent, at least along a portion thereof, to allow visualization of at least a portion of the inside of the device. A distal portion of the outer sheath may be relatively more opaque or relatively less reflective to avoid glare that may otherwise result due to the sheath reflecting light from the endoscopic light source.

31 Claims, 2 Drawing Sheets

U.S. PATENT DOCUMENTS

| | | | |
|---|---|---|---|
| 4,493,320 A | 1/1985 | Treat | |
| 4,503,855 A | 3/1985 | Maslanka | |
| 4,590,938 A | 5/1986 | Segura et al. | |
| 4,593,680 A | 6/1986 | Kubokawa | |
| 4,619,260 A | 10/1986 | Magill et al. | |
| 4,632,110 A | 12/1986 | Sanagi | |
| 4,706,656 A | 11/1987 | Kuboto | |
| 4,742,817 A | 5/1988 | Kawashima et al. | |
| 4,763,668 A | 8/1988 | Macek et al. | |
| 4,785,825 A | 11/1988 | Romaniuk et al. | |
| 4,790,831 A | 12/1988 | Skribiski | |
| D301,614 S | 6/1989 | Kozak et al. | |
| 4,840,176 A | 6/1989 | Ohno | |
| 4,840,623 A | 6/1989 | Quackenbush | |
| 4,869,238 A | 9/1989 | Opie et al. | |
| 4,872,456 A | 10/1989 | Hasson | |
| 4,905,691 A | 3/1990 | Rydell | |
| 4,942,867 A * | 7/1990 | Takahashi et al. | 600/121 |
| 4,945,920 A | 8/1990 | Clossick | |
| 4,950,232 A | 8/1990 | Ruzicka et al. | |
| 4,958,621 A * | 9/1990 | Topel et al. | 604/35 |
| 4,967,732 A | 11/1990 | Inoue | |
| 4,973,321 A | 11/1990 | Michelson | |
| 5,005,755 A | 4/1991 | Takahashi et al. | |
| 5,026,371 A | 6/1991 | Rydell et al. | |
| 5,059,199 A | 10/1991 | Okada et al. | |
| 5,066,295 A | 11/1991 | Kozak et al. | |
| 5,084,054 A | 1/1992 | Bencini et al. | |
| 5,114,403 A | 5/1992 | Clarke et al. | |
| 5,125,909 A | 6/1992 | Heimberger | |
| 5,129,913 A | 7/1992 | Ruppert | |
| 5,133,727 A | 7/1992 | Bales et al. | |
| 5,147,316 A | 9/1992 | Castillenti | |
| 5,147,373 A | 9/1992 | Ferzil | |
| RE34,110 E | 10/1992 | Opie et al. | |
| 5,156,590 A | 10/1992 | Vilmar | |
| 5,158,561 A | 10/1992 | Rydell et al. | |
| 5,163,942 A | 11/1992 | Rydell | |
| 5,176,677 A | 1/1993 | Wuchinich | |
| 5,176,702 A | 1/1993 | Bales et al. | |
| 5,179,935 A | 1/1993 | Miyagi | |
| 5,183,470 A | 2/1993 | Wetterman | |
| 5,201,740 A | 4/1993 | Nakao et al. | |
| 5,201,743 A | 4/1993 | Haber et al. | |
| 5,228,451 A | 7/1993 | Bales et al. | |
| 5,244,619 A | 9/1993 | Burnham | |
| 5,254,117 A | 10/1993 | Rigby et al. | |
| 5,254,130 A | 10/1993 | Poncet et al. | |
| 5,279,280 A | 1/1994 | Bacich et al. | |
| 5,281,220 A | 1/1994 | Blake, III | |
| 5,281,230 A | 1/1994 | Heidmeuller | |
| 5,290,294 A | 3/1994 | Cox et al. | |
| 5,318,564 A | 6/1994 | Eggers | |
| 5,334,169 A | 8/1994 | Brown et al. | |
| 5,336,227 A | 8/1994 | Nakao et al. | |
| 5,358,493 A | 10/1994 | Schweich, Jr. et al. | |
| 5,366,443 A | 11/1994 | Eggers et al. | |
| 5,376,094 A | 12/1994 | Kline | |
| 5,394,885 A | 3/1995 | Francese | |
| 5,403,342 A | 4/1995 | Tovey et al. | |
| 5,404,887 A | 4/1995 | Prather | |
| 5,406,939 A | 4/1995 | Bala | |
| 5,439,478 A | 8/1995 | Palmer | |
| 5,465,710 A | 11/1995 | Miyagi et al. | |
| 5,486,182 A | 1/1996 | Nakao et al. | |
| 5,496,292 A | 3/1996 | Burnham | |
| 5,501,692 A | 3/1996 | Riza | |
| 5,507,296 A | 4/1996 | Bales et al. | |
| 5,542,948 A | 8/1996 | Weaver et al. | |
| 5,584,843 A | 12/1996 | Wulfman et al. | |
| 5,588,964 A | 12/1996 | Imran et al. | |
| 5,591,202 A | 1/1997 | Slater et al. | |
| 5,601,533 A | 2/1997 | Hancke et al. | |
| 5,607,404 A | 3/1997 | Khairkhahan | |
| 5,636,634 A | 6/1997 | Kordis et al. | |
| 5,642,736 A | 7/1997 | Avitall | |
| 5,647,846 A | 7/1997 | Berg et al. | |
| 5,666,965 A | 9/1997 | Bales et al. | |
| 5,681,296 A | 10/1997 | Ishida | |
| 5,685,822 A | 11/1997 | Harhen | |
| 5,685,853 A | 11/1997 | Bonnet | |
| 5,707,392 A | 1/1998 | Kortenbach | |
| 5,718,360 A | 2/1998 | Green et al. | |
| 5,741,271 A | 4/1998 | Nakao et al. | |
| 5,746,747 A | 5/1998 | McKeating | |
| 5,755,724 A | 5/1998 | Yoon | |
| 5,759,187 A | 6/1998 | Nakao et al. | |
| 5,762,069 A * | 6/1998 | Kelleher et al. | 600/564 |
| 5,762,631 A | 6/1998 | Klein | |
| 5,766,217 A | 6/1998 | Christy | |
| 5,769,841 A | 6/1998 | Odell et al. | |
| 5,792,116 A | 8/1998 | Berg et al. | |
| 5,800,444 A | 9/1998 | Ridinger et al. | |
| 5,810,802 A | 9/1998 | Panescu et al. | |
| 5,814,052 A | 9/1998 | Nakao et al. | |
| 5,817,111 A | 10/1998 | Riza | |
| 5,819,738 A * | 10/1998 | Slater | 606/205 |
| 5,820,464 A | 10/1998 | Parlato | |
| 5,820,546 A | 10/1998 | Ouchi | |
| 5,827,177 A | 10/1998 | Oneda et al. | |
| 5,827,272 A | 10/1998 | Breining et al. | |
| 5,846,248 A | 12/1998 | Chu et al. | |
| 5,860,975 A | 1/1999 | Goble et al. | |
| 5,882,347 A | 3/1999 | Mouris-Laan et al. | |
| 5,885,508 A | 3/1999 | Ishida | |
| 5,901,621 A | 5/1999 | Chen | |
| 5,906,620 A | 5/1999 | Nakao et al. | |
| 5,906,621 A | 5/1999 | Secrest et al. | |
| 5,931,849 A | 8/1999 | Desvignes et al. | |
| 5,951,579 A | 9/1999 | Dykes | |
| 5,954,635 A | 9/1999 | Foley et al. | |
| 5,957,932 A | 9/1999 | Bates et al. | |
| 5,961,511 A | 10/1999 | Mortier et al. | |
| 5,971,994 A | 10/1999 | Fritzsch | |
| 5,976,130 A | 11/1999 | McBrayer et al. | |
| 5,980,519 A | 11/1999 | Hahnen et al. | |
| 5,984,904 A | 11/1999 | Steen et al. | |
| 5,984,920 A | 11/1999 | Steinbach | |
| 5,989,247 A | 11/1999 | Chambers | |
| 5,993,474 A | 11/1999 | Ouchi | |
| 6,001,096 A | 12/1999 | Bissinger et al. | |
| 6,007,560 A | 12/1999 | Gottlieb et al. | |
| 6,010,512 A | 1/2000 | Chu et al. | |
| 6,015,381 A | 1/2000 | Ouchi | |
| 6,015,415 A | 1/2000 | Avellanet | |
| 6,019,758 A | 2/2000 | Slater | |
| 6,024,708 A | 2/2000 | Bales et al. | |
| 6,027,460 A | 2/2000 | Shturman | |
| 6,036,656 A | 3/2000 | Slater | |
| 6,041,679 A | 3/2000 | Slater et al. | |
| 6,042,553 A | 3/2000 | Solar et al. | |
| 6,050,995 A | 4/2000 | Durgin | |
| 6,068,603 A | 5/2000 | Suzuki | |
| 6,071,233 A | 6/2000 | Ishikawa et al. | |
| 6,074,408 A | 6/2000 | Freeman | |
| 6,086,600 A | 7/2000 | Kortenbach | |
| 6,090,073 A | 7/2000 | Gill | |
| 6,090,108 A | 7/2000 | McBrayer et al. | |
| 6,090,129 A | 7/2000 | Ouchi | |
| 6,093,195 A | 7/2000 | Ouchi | |
| 6,099,483 A | 8/2000 | Palmer et al. | |
| 6,099,505 A | 8/2000 | Ryan et al. | |
| 6,123,678 A | 9/2000 | Palmer et al. | |
| 6,142,956 A | 11/2000 | Kortenbach et al. | |

| | | | |
|---|---|---|---|
| 6,168,571 B1 | 1/2001 | Solar et al. | |
| 6,174,292 B1 | 1/2001 | Kortenbach et al. | |
| 6,193,671 B1 | 2/2001 | Turturro et al. | |
| 6,235,026 B1 | 5/2001 | Smith | |
| 6,299,612 B1 | 10/2001 | Ouchi | |
| 6,409,727 B1 | 6/2002 | Bales et al. | |
| 6,537,205 B1 * | 3/2003 | Smith | 600/104 |

FOREIGN PATENT DOCUMENTS

| | | |
|---|---|---|
| DE | 36 16 193 A1 | 11/1986 |
| DE | 94 18 834.3 U | 3/1995 |
| DE | 199 53 359 A1 | 5/2000 |
| EP | 0 943 292 A1 | 9/1999 |
| WO | WO 92/22254 | 12/1992 |
| WO | WO 99/07288 | 2/1999 |
| WO | WO 00/42926 | 7/2000 |
| WO | WO 00/53107 | 9/2000 |
| WO | WO 01/10321 | 2/2001 |

OTHER PUBLICATIONS http://www.optinova.fi/Fluoropolymers.pbs "Medical Tubing for World Class Producers".*

Product Brochure, "TRIO 14, Re-engineering Over-The-Wire Balloon Technology," 4 pages, (1994).

* cited by examiner

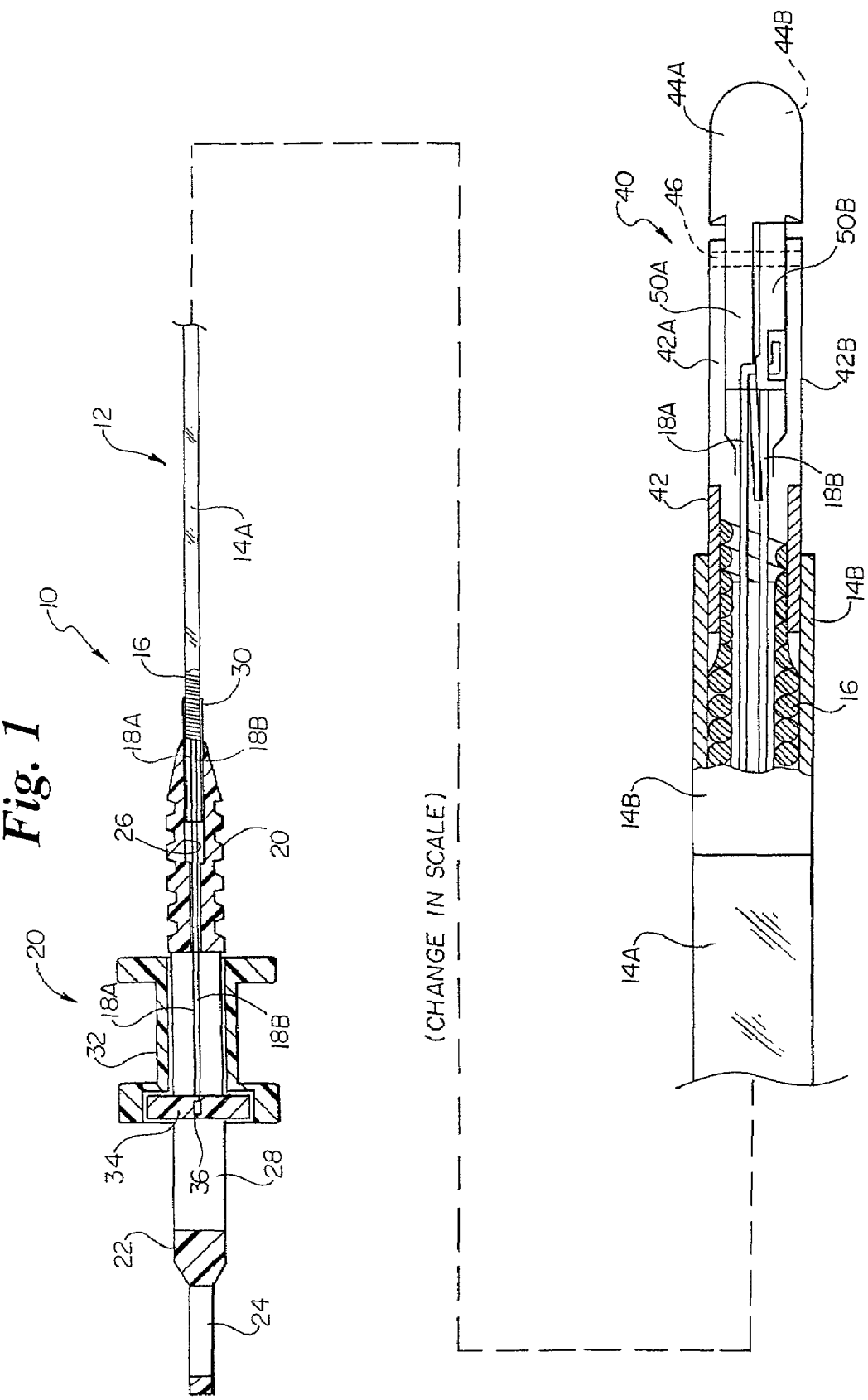

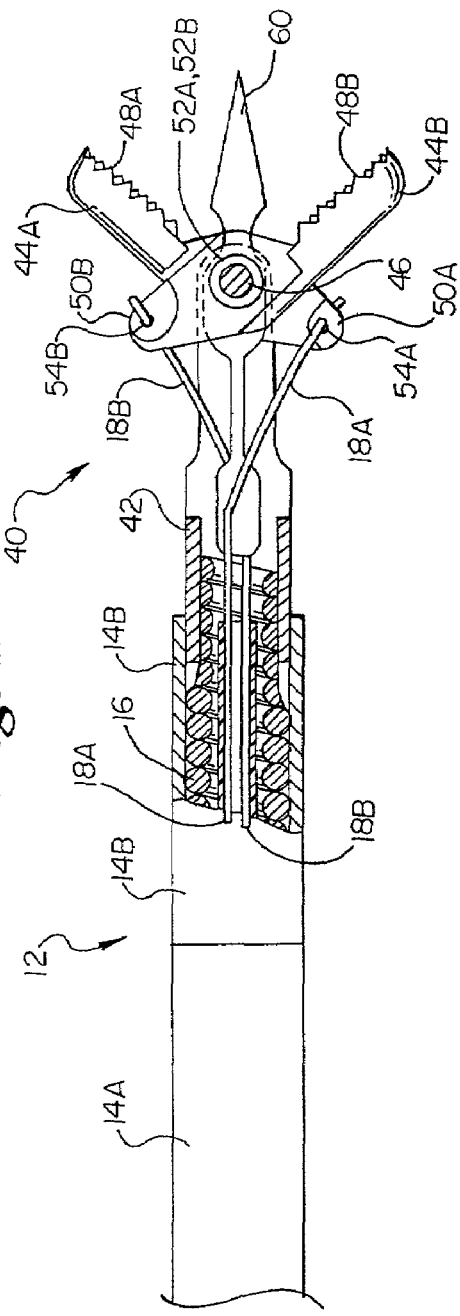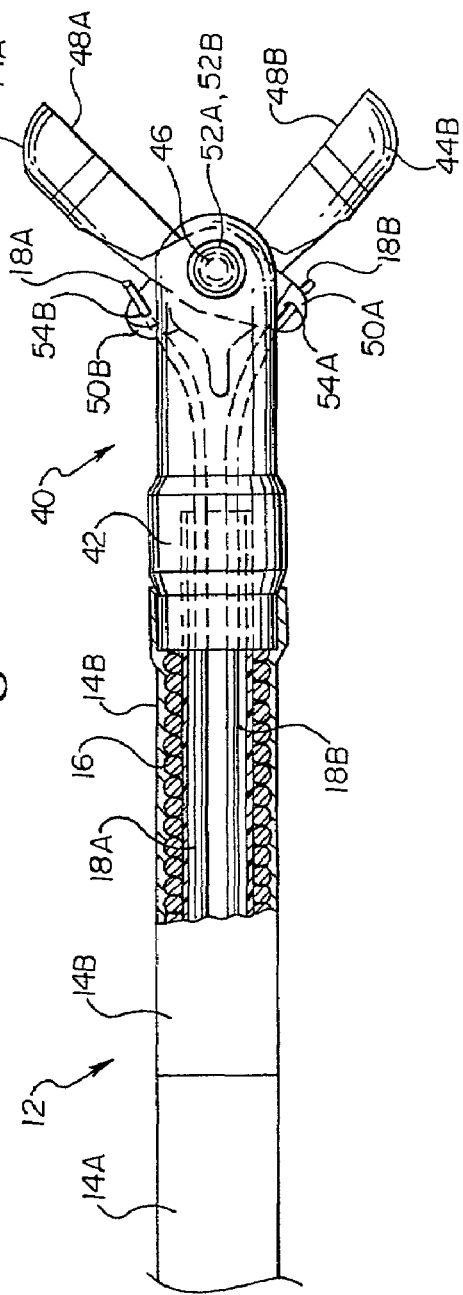

BIOPSY FORCEPS DEVICE WITH TRANSPARENT OUTER SHEATH

CROSS-REFERENCES TO RELATED APPLICATIONS

This application claims the benefit of priority to co-pending Provisional U.S. Patent Application Ser. No. 60/288,335, filed May 3, 2001 entitled BIOPSY FORCEPS DEVICE WITH TRANSPARENT OUTER SHEATH, the entire disclosure of which is herein incorporated by reference.

FIELD OF THE INVENTION

The present invention relates to endoscopic instruments. More particularly, the invention relates to biopsy forceps for use in endoscopic procedures. For purposes herein, the term "endoscopic" is to be understood in its broad sense to include laparoscopic, arthroscopic, and other microsurgical instruments whether or not used with an endoscope.

BACKGROUND OF THE INVENTION

Endoscopic biopsy forceps are medical instruments which are used in conjunction with an endoscope for taking tissue samples from the human body for analysis. These instruments typically include a long (e.g., 8 foot) slender (e.g., several millimeters in diameter) flexible coil, one or more control wires extending through the coil, a proximal actuating handle coupled to the coil and control wire(s), and a biopsy jaw assembly coupled to the distal ends of the coil and control wire(s). The actuating handle typically moves the control wire(s) relative to the coil to effect a tissue sampling operation by causing the jaws to open and close to bite a tissue sample. A known biopsy forceps instrument is disclosed in U.S. Pat. No. 5,707,392 to Kortenbach.

An endoscopic biopsy procedure is performed utilizing an endoscope which is inserted into a body and guided by manipulation to the biopsy site. The endoscope typically includes a long narrow flexible tube with an optical lens and a narrow lumen for receiving a biopsy forceps. The practitioner guides the endoscope to the biopsy site while looking through the optical lens and inserts the biopsy forceps through the lumen of the endoscope to the biopsy site. While viewing the biopsy site through the optical lens of the endoscope, the practitioner manipulates the actuating handle to effect a tissue sampling operation at the distal end of the instrument. After a sample has been obtained, the practitioner and/or an assistant carefully withdraws the instrument from the endoscope while holding the actuating handle to maintain the jaws in a closed position.

Biopsy forceps are typically designed for single use, wherein the device is discarded after its first use. In an effort to reduce expenditures, some hospitals reuse medical devices after they have been re-sterilized. Similarly, some companies sterilize used medical devices and attempt to resell them at a discount. However, the re-sterilization process is not always effective at fully cleaning biopsy forceps designed for single use. After a single use, human blood and tissue may become trapped in the biopsy forceps compromising their subsequent performance and sterility.

SUMMARY OF THE INVENTION

The present invention provides a way to discourage such reuse or confirm adequate cleaning by allowing the practitioner and/or assistant to see into the device and inspect it for trapped blood or tissue which would indicate that the device was previously used and inadequately cleaned. In some embodiments, this is accomplished by providing an outer sheath that is transparent (in the visible spectrum), at least along a proximal portion thereof. A distal portion of the outer sheath may be relatively more opaque (in the visible spectrum) to avoid glare that may otherwise result due to the sheath reflecting light from the endoscopic light source.

BRIEF DESCRIPTION OF THE DRAWINGS

FIG. 1 is a partially broken elevational view of a biopsy forceps device in accordance with an embodiment of the present invention, showing the jaw in the closed position;

FIG. 2 is a is a partially broken elevational view of a distal portion of the biopsy forceps device shown in FIG. 1, showing an example of a jaw having serrated edges in the open position; and FIG. 3 is a is a partially broken elevational view of a distal portion of the biopsy forceps device shown in FIG. 1, showing an example of a jaw having straight cutting edges in the open position.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Refer now to FIG. 1 which illustrates a partially broken elevational view of a biopsy forceps device 10 in accordance with an embodiment of the present invention. The biopsy forceps device 10 includes an elongate shaft 12 having a flexible coil 16 covered by an outer polymeric sheath 14. Polymeric sheath 14 is designed to allow a clinician to easily determine if device 10 had been used previously and/or if device 10 has been adequately cleaned and sterilized.

The polymeric outer sheath 14 can include a proximal portion 14A and a distal portion 14B. The lengths of the respective portions may be varied in different embodiments. For example, the length of the distal portion 14B may correspond to the length of the biopsy forceps device 10 which extends beyond the distal end of the endoscope. Moreover, in some embodiments, the composition or properties of the proximal portion 14A and the distal portion 14B may differ. Alternatively, the composition or properties may be the same or similar.

Polymeric sheath 14 may comprise polytetrafluoroethylene (PTFE), fluorinated ethylene propylene (FEP), polyolefin, polyethylene, polycarbonate, or other suitable polymer material. In some embodiments, all or a portion of proximal portion 14A does not include any colorant such that it remains substantially transparent. This allows the physician and/or assistant to inspect the inner workings of the elongate shaft 12 for foreign material and proper function. If foreign material, such as blood and/or tissue, appears under the transparent outer sheath 14A, the physician and/or assistant will be able to ascertain that the device 10 was previously used and insufficiently cleaned.

In some embodiments, the entire length of outer sheath 14 (i.e., both proximal portion 14A and distal portion 14B) may be comprised of substantially transparent materials. Alternatively, only a distal portion 14B may be substantially transparent. However, it may be beneficial to alter the relative opacity of the polymeric sheath 14 in some uses. For example, if the transparent material of the proximal sheath portion 14A were utilized in the distal sheath portion 14B, the transparent material may create a halo effect during certain endoscopic visualization procedures. In particular, because the distal shaft portion 14B may extend beyond the distal end of the endoscope, light emitted from the light source may tend to reflect off the distal sheath portion 14B if a transparent material is used, thereby creating glare which appears as a halo during visualization. This halo effect may interfere with the ability of the physician to distinguish between different colors and, therefore, compromise the ability of the physician to distinguish between different types of tissue being sampled.

To reduce the potential halo effect, the distal sheath portion 14B may be made relatively more opaque or relatively less reflective to visible light than the proximal shaft portion 14A. Thus, the material or surface of the distal portion 14B, relative to the proximal portion 14A, may have modified pigmentation (color) or surface finish, which affect the opaqueness or reflectivity of the distal portion 14B. As used herein, reflectivity is defined as the ratio of the light reflected from a surface to the total incident light. For example, the color of the distal portion 14B may be black and the surface finish of the distal portion 14B may be matte. The reflectivity of the distal portion 14B may be less than about 0.50, preferably less than about 0.25, and ideally less than about 0.10.

The relatively high opaqueness or relatively low reflectivity of the distal portion 14B may be provided by a number of means. In one embodiment, the distal portion 14B comprises an extension of the proximal portion 14A (e.g., a continuous homogenous extrusion) with a polymeric sleeve or coating disposed on the outside surface of the distal portion 14B. An example of a suitable outer sleeve comprises a thin heat shrinkable tube made from a polymer mixed with a black colorant (e.g., black iron oxide). An example of a suitable coating comprises a permanent biocompatible black ink. Such outer sleeve or coating may have a relatively dark color (e.g., black) and a relatively low glare surface finish. The same type of polymeric sleeve or coating may be applied to the inside surface of the distal portion 14B if the distal portion 14B otherwise comprises a relatively transparent material.

In another embodiment, the proximal portion 14A and distal portion 14B are integrally formed by an alternating extrusion process or co-extrusion process. In this embodiment, the proximal portion 14A and distal portion 14B are formed in the same extrusion process wherein the proximal portion 14A is formed by an extruded transparent polymer and the distal portion 14B is formed by switching to an extruded opaque polymer. The opaque polymer may comprise the same transparent polymer loaded with a colorant or a different, but compatible, polymer loaded with a colorant.

In yet another embodiment, the distal portion 14B comprises a separate tubular element thermally or adhesively bonded to the proximal portion 14A. In this embodiment, the distal portion 14B comprises an extruded opaque polymer tube segment or a tube segment having an opaque sleeve or opaque coating as discussed previously. Those skilled in the art will recognize that there are other suitable manufacturing processes conventional in the art to provide a functional distal sheath portion 14B.

A distal effector assembly 40 is connected to the distal end of the elongate shaft 12. Any one of a number of effector assemblies could be used without departing from the spirit of the invention. For example, effector assembly 40 may generally comprise a diagnostic or therapeutic device such as a biopsy device, a loop or snare, a cutting device, a needle or penetrating device, a device for delivering energy (such as cutting or ablating energy), an imaging device, a drug-delivery device, etc. In FIG. 1, the distal effector assembly 40 is shown as a biopsy forceps in a closed position, and in FIGS. 2 and 3, the distal effector assembly 40 is shown in the open position.

In some embodiments, a pair of control wires 18A,18B are disposed in the flexible coil 16 extending through the elongate shaft 12. The control wires 18A,18B are axially displaceable relative to the flexible coil 16 and the outer sheath 14. The proximal end of the control wires 18A,18B are operably coupled to a proximal handle assembly 20 connected to the proximal end of the elongate shaft 12. The distal ends of the control wires 18A,18B are operably coupled to the distal effector assembly 40. With this arrangement, the handle assembly 20 may be used to actuate the control wires 18A,18B, which in turn actuate the distal effector assembly 40.

The proximal handle assembly 20 includes a central shaft portion 22, the proximal end of which includes a thumb ring 24, and the distal end which includes a longitudinal bore 26. A strain relief 30 extends across the junction between the proximal end of the elongate shaft 12 and the distal end of the proximal handle assembly 20. A longitudinal slot 28 extends from the proximal end of the bore 26 to a point distal of the thumb ring 24. The proximal handle assembly 20 also includes a displaceable spool 32 having a cross member 34 which passes through the slot 28 in the central shaft 22. The cross member 34 includes a coupling means 36 for attaching the proximal ends of the control wires 18A,18B.

Refer now additionally to FIGS. 2 and 3 which illustrate partially broken elevational views of two different embodiments of a distal portion of the biopsy forceps device 10 shown in FIG. 1. The embodiment illustrated in FIG. 2 shows a pair of jaws including serrated edges and a flat cutting knife. The embodiment illustrated in FIG. 3 shows a pair of jaws having straight cutting edges without a cutting knife.

The distal effector assembly 40 includes a clevis 42 coupled to the distal end of the elongate coil 16. The clevis 42 is coupled to a pair of forceps jaws 44A,44B. The clevis 42 includes a pair of clevis arms 42A,42B (see FIG. 1) between which the jaws 44A,44B are rotatably mounted on an axle pin 46. Each jaw member 44A,44B includes a distal cutting edge 48A,48B, a proximal tang 50A,50B, and a mounting hole 52A,52B. The proximal tangs 50A,50B are each coupled to the distal end of their respective control wires 18A,18B, by way of holes 54A,54B in the respective tangs 50A,50B. With this arrangement, relative longitudinal movement between the central shaft 22 and the spool 32 of the proximal handle assembly 20 results in longitudinal movement of the control wires 18A,18B relative to the coil 16, such that the jaws 44A,44B open and close, depending on the direction of relative movement.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A biopsy forceps device, comprising:
   an elongate shaft having a proximal end and a distal end;
   an effector assembly comprising a pair of jaws connected to the distal end of the elongate shaft;
   a handle connected to the proximal end of the elongate shaft and operably connected to the effector assembly for actuation thereof; and
   a polymer sheath disposed about the elongate shaft, the polymer sheath having a transparent portion to permit visualization of the shaft therethrough;
   wherein the polymer sheath includes a proximal portion and a distal portion, wherein the distal portion of the sheath is relatively more opaque than the proximal portion of the sheath to reduce glare.

2. A biopsy forceps device as in claim 1, wherein the relatively more opaque distal portion comprises a polymeric sleeve disposed about the sheath.

3. A biopsy forceps device as in claim 1, wherein the relatively more opaque distal portion comprises a coating disposed about the sheath.

4. A biopsy forceps device as in claim 1, wherein the relatively more opaque distal portion comprises a dark colorant disposed in the sheath.

5. A biopsy forceps device as in claim 1, wherein the relatively more opaque distal portion is black.

6. A biopsy forceps device as in claim 5, wherein the relatively more opaque distal portion has a matte surface finish.

7. A biopsy forceps device, comprising:
   an elongate shaft having a proximal end and a distal end;
   an effector assembly comprising a pair of jaws connected to the distal end of the elongate shaft;
   a handle connected to the proximal end of the elongate shaft and operably connected to the effector assembly for actuation thereof; and
   a polymer sheath disposed about the elongate shaft, the polymer sheath having a proximal portion and a distal portion, wherein at least the proximal portion includes a transparent section to permit visualization of the elongate shaft therein;
   wherein the distal portion of the sheath has a lower reflectivity than the proximal portion of the sheath to reduce glare.

8. A biopsy forceps device as in claim 7, wherein the reflectivity of the distal portion of the sheath is less than 0.50.

9. A biopsy forceps device as in claim 7, wherein the reflectivity of the distal portion of the sheath is less than 0.25.

10. A biopsy forceps device as in claim 7, wherein the reflectivity of the distal portion of the sheath is less than 0.10.

11. A biopsy forceps device as in claim 7, wherein the low reflectivity distal portion comprises a polymeric sleeve disposed about the sheath.

12. A biopsy forceps device as in claim 7, wherein the low reflectivity distal portion comprises a coating disposed about the sheath.

13. A biopsy forceps device as in claim 7, wherein the low reflectivity distal portion comprises a dark colorant disposed in the sheath.

14. A biopsy forceps device as in claim 7, wherein the low reflectivity distal portion is black.

15. A biopsy forceps device as in claim 14, wherein the low reflectivity distal portion has a matte surface finish.

16. A biopsy forceps device, comprising:
    an elongate shaft having a proximal end and a distal end;
    an effector assembly comprising a pair of jaws connected to the distal end of the elongate shaft;
    a handle connected to the proximal end of the elongate shaft and operably connected to the effector assembly for actuation thereof; and
    a polymer sheath disposed about the elongate shaft, wherein at least a portion of the polymer sheath is transparent;
    wherein the polymer sheath includes a proximal portion and a distal portion, and wherein the proximal portion is transparent and the distal portion is opaque.

17. The biopsy forceps device in accordance with claim 16, wherein the distal portion includes a polymeric sleeve disposed over the sheath.

18. The biopsy forceps device in accordance with claim 16, wherein the distal portion of the sheath includes a generally dark colorant.

19. The biopsy forceps device in accordance with claim 16, wherein the distal portion of the sheath has a matte finish.

20. An biopsy forceps device, comprising:
    an elongate shaft including a proximal end and a distal end;
    wherein a flexible coil is disposed about at least a portion of the shaft;
    an effector assembly comprising a pair of jaws connected to the distal end of the elongate shaft;
    a handle connected to the proximal end of the elongate shaft and operably connected to the effector assembly for actuation thereof; and
    a polymer sheath disposed about the coil, wherein at least a portion of the polymer sheath is transparent;
    wherein the polymer sheath includes a proximal portion and a distal portion, and wherein the proximal portion is transparent and the distal portion is generally opaque.

21. The biopsy forceps device in accordance with claim 20, wherein the distal portion includes a polymeric sleeve disposed over the sheath.

22. The biopsy forceps device in accordance with claim 20, wherein the distal portion of the sheath includes a generally dark colorant.

23. The biopsy forceps device in accordance with claim 20 wherein the distal portion of the sheath has a matte finish.

24. A biopsy forceps device, comprising:
    an elongate shaft having a proximal end and a distal end;
    an effector assembly connected to the distal end of the elongate shaft;
    a handle connected to the proximal end of the elongate shaft and operably connected to the effector assembly for actuation thereof;
    a first control wire having a proximal end coupled to the handle and a distal end coupled to the effector;
    a second control wire having a proximal end coupled to the handle and a distal end coupled to the effector; and
    a polymer sheath disposed about the elongate shaft, wherein at least a portion of the polymer sheath is transparent;
    wherein the polymer sheath includes a proximal portion and a distal portion, and wherein the proximal portion is transparent and the distal portion is generally opaque.

25. The biopsy device in accordance with claim 24, wherein the first control wire and the second control wire are disposed within the shaft.

26. The biopsy device in accordance with claim 25, wherein the shaft includes a flexible coil and wherein the first control wire and the second control wire are disposed within the coil.

27. The biopsy device in accordance with claim 24, wherein the effector includes a clevis.

28. The biopsy device in accordance with claim 27, wherein the clevis includes a first jaw member coupled to the first control wire and a second jaw member coupled to the second control wire.

29. The biopsy forceps device in accordance with claim 24, wherein the distal portion includes a polymeric sleeve disposed over the sheath.

30. The biopsy forceps device in accordance with claim 24, wherein the distal portion of the sheath includes a generally dark colorant.

31. The biopsy forceps device in accordance with claim 24, wherein the distal portion of the sheath has a matte finish.

* * * * *